United States Patent von Mallek

[11] Patent Number: 5,997,854
[45] Date of Patent: *Dec. 7, 1999

[54] CONDITIONING SHAMPOO FORMULATION

[75] Inventor: Peter von Mallek, San Juan, Puerto Rico

[73] Assignee: Henkel Corporation, Gulph Mills, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/763,271

[22] Filed: Dec. 10, 1996

[51] Int. Cl.⁶ .................................................. A61K 7/075
[52] U.S. Cl. ..................................... 424/70.19; 424/70.21; 424/70.27; 424/70.28; 424/70.24; 424/70.31
[58] Field of Search ........................... 424/70.19, 70.28, 424/70.31, 70.21, 70.27, 70.24

[56] References Cited

U.S. PATENT DOCUMENTS

| | | | |
|---|---|---|---|
| 5,266,690 | 11/1993 | McCurry, Jr. et al. | 536/18.6 |
| 5,296,622 | 3/1994 | Uphues et al. | 554/103 |
| 5,478,562 | 12/1995 | Cauwet | 424/70.31 |
| 5,494,659 | 2/1996 | Salka | 424/70.13 |
| 5,514,369 | 5/1996 | Salka | 424/70.1 |
| 5,534,248 | 7/1996 | Matsuo | 424/70.31 |
| 5,670,471 | 9/1997 | Amalric | 424/70.31 |
| 5,679,331 | 10/1997 | Hague | 424/70.19 |

Primary Examiner—Thurman K. Page
Assistant Examiner—Todd D. Ware
Attorney, Agent, or Firm—Wayne C. Jaeschke; John E. Drach; Steven J. Trzaska

[57] ABSTRACT

A hair conditioning shampoo composition containing: (a) a quaternary ammonium component; (b) an emulsifier component; (c) an amphoteric surfactant component; (d) an alkyl polyglycoside of formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; (e) an emollient component; (f) water; (g) an anionic surfactant component; (h) an amide component; and (i) an electrolyte component.

42 Claims, No Drawings

CONDITIONING SHAMPOO FORMULATION

FIELD OF THE INVENTION

The present invention generally relates to conditioning shampoos having improved hair conditioning properties. More particularly, due to the inclusion of a quaternary ammonium compound and a Guerbet alcohol, enhanced conditioning of hair can be obtained in the absence of silicones.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing relates to the cleaning of hair by removing excess soil and sebum. However, the shampooing process has disadvantages in that the hair is left in a wet, tangled and generally unmanageable state. A variety of approaches have been developed to alleviate the after-shampoo problems. These approaches range from the inclusion of hair conditioning aids in shampoos to post-shampoo application of hair conditioners, i.e., hair rinses. Hair rinses typically work by depositing a polymeric film or other material onto the hair. However, such solutions to a very prevalent problem have not been fully satisfactory for the following reasons. Hair rinses are generally liquid in nature and must be applied in a separate step following the shampooing step, left on the hair for a length of time, and rinsed with fresh water. This, of course, is time consuming and is not convenient.

While shampoos have been disclosed which contain conditioning aids, they have not been totally satisfactory for a variety of reasons. One problem relates to compatibility problems between good cleaning anionic surfactants and the fatty cationic agents which are good conditioning agents. This has caused other surfactants such as nonionics, amphoterics and zwitterionics to be experimented with by the shampoo industry.

The use of these other surfactants solved many of the compatibility problems but still did not provide complete answers in all areas. For instance cationic conditioners may not deliver the required level of softness desired by users. Materials which have been found to increase softness are silicones, both those which are soluble as well as insoluble in the shampoo matrix.

Even with the inclusion of silicones, one unsolved problem is that of providing satisfactory static control as well as other hair conditioning properties such as softness and wet and dry combability. Moreover, the use of silicones in shampoo formulations has certain inherent disadvantages such as: (1) silicones act as defoamers, thus reducing the amount of foam (lather) formed during the hair washing process; (2) silicones are prone to leave an undesirable residue on the hair, even after rinsing, which cause the hair to be unnecessarily weighed down; (3) the undesirable residue imparted onto the hair by the silicones, has a tendency to quickly attract dirt particles present in the environment, thus making the hair unseemingly dirty/greasy looking; and (4) silicones are typically difficult to incorporate into formulations due to their inherent chemical incompatability with many of the components contained therein.

SUMMARY OF THE INVENTION

The present invention is directed to a process for making a hair conditioning shampoo composition involving the steps of:

(i) forming a primary formulation by combining, at a temperature of from about 75° C. up to 80° C.:
  (a) a quaternary ammonium component;
  (b) an emulsifier component;
  (c) an amphoteric surfactant component;
  (d) an alkyl polyglycoside of formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6;
  (e) an emollient component; and
  (f) water;
(ii) forming a secondary formulation by cooling the primary formulation to a temperature of from about 70 to about 30° C. and then adding, with mixing:
  (g) an anionic surfactant component;
  (h) an amide component; and
  (i) an electrolyte component; and
(iii) cooling the secondary formulation to room temperature, thus forming a finished hair conditioning shampoo composition.

The present invention is also directed to a hair conditioning shampoo composition containing:
  (a) a quaternary ammonium component;
  (b) an emulsifier component;
  (c) an amphoteric surfactant component;
  (d) an alkyl polyglycoside of formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6;
  (e) an emollient component;
  (f) water;
  (g) an anionic surfactant component;
  (h) an amide component; and
  (i) an electrolyte component.

The present invention is also directed to a process for simultaneously washing and conditioning hair by contacting the hair with the above-disclosed hair conditioning shampoo composition.

DESCRIPTION OF THE INVENTION

Other than in the operating examples, or where otherwise indicated, all numbers expressing quantities of ingredients and/or reaction conditions are to be understood as being modified in all instances by the term "about".

The quaternary ammonium compounds employed in the hair conditioning shampoo composition of the present invention impart anti-static and improved combability properties onto the hair treated therewith. While any type of quaternary ammonium compound such as, for example, a quaternary ammonium salt, may be employed, quaternized esters are particularly preferred.

Quaternized esters are generally obtainable by reacting fatty acids with alkanolamines, followed by quaternization of the reaction products with an alkylating agent. Examples of quaternized esters which may be employed in the present invention, and methods of making them, can be found in U.S. Pat. No. 5,296,622, the entire contents of which is hereby incorporated by reference. In a particularly preferred embodiment of the present invention, the quaternary ammonium compound employed is a dipalmitoleyl ethyl hydroxyethyl ammonium methyl sulfate. The quaternary ammonium compound may be present in the composition in an amount ranging from about 0.5 to about 1.5% by weight, and preferably from about 0.8 to about 1.0% by weight, based on the weight of the composition.

The alkyl polyglycosides which can be used in the compositions according to the invention have the formula I $$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:
1. APG® 225 Surfactant—an alkyl polyglycoside in which the alkyl group contains 8 to 10 carbon atoms and having an average degree of polymerization of 1.7.
2. GLUCOPON® 425 Surfactant—an alkyl polyglycoside in which the alkyl group contains 8 to 16 carbon atoms and having an average degree of polymerization of 1.48.
3. GLUCOPON® 625 Surfactant—an alkyl polyglycoside in which the alkyl groups contains 12 to 16 carbon atoms and having an average degree of polymerization of 1.6.
4. APG® 325 Surfactant—an alkyl polyglycoside in which the alkyl group contains 9 to 11 carbon atoms and having an average degree of polymerization of 1.5.
5. GLUCOPON® 600 Surfactant—an alkyl polyglycoside in which the alkyl group contains 12 to 16 carbon atoms and having an average degree of polymerization of 1.4.
6. PLANTARENG® 2000 Surfactant—a $C_{8-16}$ alkyl polyglycoside in which the alkyl group contains 8 to 16 carbon atoms and having an average degree of polymerization of 1.4.
7. PLANTAREN® 1200 Surfactant—an alkyl polyglycoside in which the alkyl group contains 12 to 16 carbon atoms and having an average degree of polymerization of 1.4.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

A particularly preferred alkyl polyglycoside of formula I which may be employed in the present invention is one wherein $R_1$ is a monovalent organic radical having from about 12 to about 16 carbon atoms, b is zero, and a is a number having a value of about 1.4. The alkyl polyglycoside component may be present in the composition in an amount of from about 2 to about 10% by weight, and preferably from about 5 to about 7% by weight.

Examples of amphoteric surfactants which can be used in the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, and N-alkyltaurines such as the one prepared by reacting dodecylamine with sodium isethionate. Particularly preferred amphoteric surfactants are betaines such as, for example, coco-amidopropyl betaines. The amphoteric surfactant component may be present in the composition in an amount ranging from about 5 to about 15% by weight, and preferably from about 9 to about 12% by weight, based on the weight of the composition.

Synthetic anionic detergents useful herein include alkyl and alkyl ether sulfates. These materials have the respective formulae $R_3OSO_3M$ and $R_3O(C_2H_4O)_xSO_3M$ wherein $R_3$ is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 14 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl trioxyethylene sulfate; lithium tallow alkyl trioxyethylene sulfate; sodium tallow alkyl hexaoxyethylene sulfate; and sodium lauryl ether sulfate.

Additional examples of anionic synthetic detergents which come within the terms of the present invention are the reaction product of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil.

Still other anionic synthetic detergents include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-cicosene and 1-tetraeosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another suitable class of anionic surfactants are the water-soluble salts of the organic, sulfuric acid reaction products of the formula:

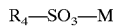

$R_4$—$SO_3$—M wherein $R_4$ is chosen from the group consisting of a straight or branched chain, saturated aliphatic hydrocarbon radial having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Particularly preferred anionic surfactants are sodium lauryl ether sulfates having from 2 to 3 moles of ethylene oxide. The anionic surfactant component may be present in the composition in an amount ranging from about 5 to about 10% by weight, and preferably from about 7 to about 8% by weight, based on the weight of the composition.

Examples of amides which may be employed in the present invention have the general formula II:

(II)

wherein $R_3$ is an alkyl group containing from about 8 to about 18 carbon atoms and each $R_4$ is the same or different and is selected from the group consisting of hydrogen, $C_{1-3}$ alkyl, $C_{1-3}$ alkanol, and —($C_2H_4O$—), and mixtures thereof. Examples of amides suitable for use in the present invention include, but are not limited to, derivatives of monoethanolamides and diethanolamides. A particularly preferred amide for use in the present invention is cocamide-diethanolamide, commercially available from Henkel Corporation, Ambler, Pa., under the tradename STANDAMID® KD. The amide component may be present in the composition in an amount ranging from about 0.5 to about 3.0% by weight, and preferably from about 1.5 to about 2.0% by weight, based on the weight of the composition.

The use of an emulsifier is essential in the present invention so that the various components employed therein may form a single, emulsified hair conditioning shampoo composition. Examples of suitable emulsifiers which may be employed in the present invention include, but are not limited to, alkoxylated fatty alcohols and alkoxylated fatty acid esters, such as polysorbates. A particularly preferred emulsifier is cetyryl alcohol having about 20 moles of ethylene oxide. The emulsifier component may be present in the composition in an amount ranging from about 0.5 to about 2.0% by weight, and preferably from about 0.8 to about 1.0% by weight, based on the weight of the composition.

Yet another essential component of the present invention is an emollient component used to impart emolliency properties to the hair conditioning shampoo. Examples of suitable compounds which may be used as emollients in the present invention include, but are not limited to, fatty alcohols and fatty alcohol derivatives.

Fatty alcohols are monofunctional, usually straight-chain-saturated or unsaturated alcohols with chain lengths between $C_6$ and $C_{24}$. These high molecular weight alcohols are produced synthetically by the Oxo and Ziegler processes. Other methods of production include reduction of vegetable seed oils and their fatty acids with sodium, catalytic hydrogenation at elevated temperatures and pressures, and hydrolysis of spermaceti and sperm oil by saponification and vacuum fractional distillation.

Examples of suitable compounds which may be employed as emollients in the present invention include, but are not limited to, fatty acid esters such as octyl stearate, myreth-3-myristate, hexyldecyl stearate, octyldodecyl stearate, PEG-7-glyceryl cocoate, oleyl erucate, coco caprylate/caprate, myristyl myristate, shea butter, cetearyl isononanoate, decyl oleate, isopropyl myristate, isopropyl palmitate, butyl stearate, propylene glycol isostearate, propylene glycol dipelargonate, caprylic/capric triglyceride, and propylene glycol dicaprylate/dicaprate.

Branched fatty alcohols and fatty alcohol derivatives may also be employed as emollients in accordance with the present invention. Examples of suitable branched fatty alcohols used as emollients include, but are not limited to, octyl dodecanol, and hexyldecanol, commonly known as Guerbet alcohols.

Other examples of emollient components which may be employed include dicapryl ether and dioctyl cyclohexane.

In a particularly preferred embodiment of the present invention, the emollient employed is a Guerbet alcohol selected from the group consisting of 2-hexyl decanol, 2-octyl decanol, 2-hexyl dodecanol, 2-octyl dodecanol and mixtures thereof. The emollient component may be present in the composition in an amount ranging from about 0.5 to about 2.0% by weight, and preferably from about 0.8 to about 1.0% by weight, based on the weight of the composition.

Another component present in the hair conditioning shampoo composition of the present invention is an electrolyte which is used in order to increase the viscosity of the composition. Examples of suitable electrolytes include, but are not limited to, salts such as sodium and potassium chloride. The electrolyte component may be present in the composition in an amount ranging from about 0.5 to about 2.0% by weight, and preferably from about 1.0 to about 1.5% by weight, based on the weight of the composition.

Water is the last essential component of the present invention and forms the remainder of the composition.

The hair conditioning shampoo of the present invention may contain a variety of non-essential, optional components suitable for rendering the composition more desirable. These optional components are well known to those skilled in the art. Examples thereof include, but are not limited to, formaldehyde-free preservatives such as benzyl alcohol, methyl paraben, propyl paraben, imidazolidinyl urea and, preferably, $5-NO_2$, 5-Br dioxane; perfumes; dyes; pearlescents; and the like. The amount of optional additive component(s) present in the composition will vary, depending on the aesthetic properties that are sought by both the industry and consumers. The specific additives and the amounts employed will ultimately be determined by those skilled in the art. The hair conditioning shampoo composition of the present invention will, in general, have a viscosity in the range of from about 3,500 to 6,000 cps, and preferably from about 4,000 to about 6,000 cps.

The crux of the present invention relates to the surprising discovery that by combining one of the above-disclosed emollient components and a quaternary ammonium compound, hair conditioning properties similar to those imparted by silicones may be obtained, without the attendant disadvantages associated with the use of silicones. Thus, the present invention provides for the formulation of a silicone-free hair conditioning shampoo composition.

According to one embodiment of the present invention, there is thus provided a hair conditioning shampoo composition containing: (a) from about 0.8 to about 1.0% by weight of a quaternized ester, preferably dipalmitoleyl ethyl hydroxyethyl ammonium methyl sulfate; (b) from about 5 to about 7% by weight of an alkyl polyglycoside of formula I, preferably one wherein $R_1$ is a monovalent organic radical having from about 12 to about 16 carbon atoms, b is zero, and a is a number having a value of about 1.4; (c) from about 9 to about 12% by weight of an amphoteric surfactant, preferably a betaine; (d) from about 0.8 to about 1.0% by weight of an emulsifier, preferably a cetyryl alcohol having 20 moles of ethylene oxide; (e) from about 0.8 to about 1.0% by weight of an emollient, preferably a Guerbet alcohol; (f) from about 7 to about 8% by weight of an anionic surfactant, preferably sodium lauryl ether sulfate having from 2–3 moles of ethylene oxide; (g) from about 1.5 to about 2.0% by weight of an amide component, preferably a cocamide diethanolamide; (h) from about 1.0 to about 1.5% by weight of an electrolyte, preferably sodium chloride; (i) from about 0.1 to about 1.0% by weight of a formaldehyde-free preservative, preferably a polysorbate; (j) from about 0.1 to about 1.0% by weight of a perfume; (k) from about 1.5 to about 2.0% by weight of a pearlescent; and (1) remainder, water, all weights being based on the weight of the hair conditioning shampoo composition.

According to another embodiment of the present invention, there is provided a process for making the above-disclosed hair conditioning shampoo. The process involves combining the above-disclosed components in three distinct phases, in order that a fully dispersed, homogeneous composition may be formed.

The first phase involves forming a primary formulation by combining: (a) a quaternary ammonium compound, (b) an amphoteric surfactant, (c) an alkyl polyglycoside, (d) an emollient, (e) an emulsifier, and (f) water, with stirring, at a temperature ranging from about 75° C. up to a maximum of 80° C., until a homogeneous mixture is formed. It should be noted that the temperature during the formation of the primary formulation should not exceed 80° C. The use of a temperature above 80° C. results in a significant drop in the viscosity of the composition, thereby rendering it ineffective. once a homogeneous mixture is formed, the second phase involves forming a secondary formulation by cooling the homogeneous primary formulation to a temperature of from about 70 to about 30° C., at which time (g) an electrolyte, (h) an anionic surfactant, (i) an amide and, optionally, (j) a preservative, are added, with stirring, to the cooled primary formulation. Phase three involves further cooling the secondary formulation to room temperature, thus forming the hair conditioning shampoo composition of the present invention. If desired, additives such as pearlescents and perfumes may be added to the hair conditioning shampoo composition, at room temperature, with stirring, in order to make the composition more aesthetically desirable to consumers.

It is important that the hair conditioning shampoo composition be formulated, per the above process, so that a homogeneous composition may be formed. Due to the quantity and variety of components used in formulating the hair conditioning shampoo of the present invention, the difficulty in combining them to form a user-friendly system is significant. However, by employing the above-disclosed phases, their successful combination is achieved.

According to yet another embodiment of the present invention, there is provided a process for simultaneously washing and conditioning hair by contacting the hair with the above-disclosed hair conditioning shampoo composition.

These and other aspects of the present invention will be better understood from the examples which follow, all of which are meant to be illustrative only, and not meant to unduly limit the scope of the present invention in any way.

EXAMPLE

A hair conditioning shampoo composition in accordance with the present invention was formulated as follows.

Phase 1

A primary formulation was prepared having the following components:

| Component | %/wt. |
|---|---|
| (a) DEHYQUART ® 4046 | 0.8 |
| (b) EUMULGIN ® B2 | 0.8 |
| (c) EUTANOL ® G | 0.8 |
| (d) DEHYTON ® AB30 | 9.0 |
| (e) PLANTAREN ® 1200 | 5.0 |
| (f) water | 51.2 |
| | 87.6 |

Components (a)–(f) were combined, with stirring, at a temperature of about 75° C., for a period of time sufficient enough to form a homogeneous mixture.

Phase 2

A secondary hair conditioning shampoo composition was then prepared by first lowering the temperature of the primary hair conditioning shampoo composition to about 30° C., followed by the addition of the following components:

| Component | %/wt. |
|---|---|
| (g) NaCl | 1.5 |
| (h) TEXAPON ® N70 | 7.0 |
| (i) water | 20.0 |
| (j) STANDAMID ® KD | 1.5 |
| (k) BRONIDOX ® L | 0.2 |
| | 97.8 |

Components (g)–(k) were combined, with stirring, at a temperature of about 30° C., for a period of approximately 30 minutes to form the secondary composition.

Phase 3

The secondary hair conditioning shampoo composition was then cooled to room temperature, after which the following components were added:

| Component | %/wt. |
|---|---|
| (l) EUPERLAN ® PK-771 | 2.0 |
| (m) perfume | 0.2 |
| | 100.0 |

What is claimed is:

1. A hair conditioning shampoo composition comprising:
   (a) a quaternary ammonium component;
   (b) an emulsifier component;
   (c) an amphoteric surfactant component;
   (d) an alkyl polyglycoside of formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6;
   (e) an emollient component;
   (f) water;
   (g) an anionic surfactant component;
   (h) an amide component; and
   (i) an electrolyte component.

2. The composition of claim 1 wherein the quaternary ammonium component is a quaternized ester.

3. The composition of claim 2 wherein the quaternized ester is a dipalmitoleyl ethyl hydroxyethyl ammonium methyl sulfate.

4. The composition of claim 1 wherein the quaternary ammonium component is present in the composition in an amount of from about 0.5 to about 1.5% by weight, based on the weight of the composition.

5. The composition of claim 1 wherein the emulsifier is an alkoxylated fatty alcohol.

6. The composition of claim 5 wherein the ethoxylated fatty alcohol is a cetearyl alcohol having 20 moles of ethylene oxide.

7. The composition of claim 1 wherein the emulsifier component is present in the composition in an amount of from about 0.5 to about 2.0% by weight, based on the weight of the composition.

8. The composition of claim 1 wherein the amphoteric surfactant component is a betaine.

9. The composition of claim 1 wherein the amphoteric surfactant component is present in the composition in an amount of from about 5 to about 15% by weight, based on the weight of the composition.

10. The composition of claim 1 wherein in formula I $R_1$ is a monovalent organic radical having from about 12 to about 16 carbon atoms, b is zero, and a is a number having a value of about 1.4.

11. The composition of claim 1 wherein the alkyl polyglycoside is present in the composition in an amount of from about 2 to about 10% by weight, based on the weight of the composition.

12. The composition of claim 1 wherein the emollient component is a Guerbet alcohol.

13. The composition of claim 12 wherein the Guerbet alcohol is octyl dodecanol.

14. The composition of claim 1 wherein the anionic surfactant component is sodium lauryl ether sulfate having from 2 to 3 moles of ethylene oxide.

15. The composition of claim 1 wherein the anionic surfactant component is present in the composition in an amount of from about 5 to about 10% by weight, based on the weight of the composition.

16. The composition of claim 1 wherein the amide component is cocamide diethanolamide.

17. The composition of claim 1 wherein the amide component is present in the composition in an amount of from about 0.5 to about 3% by weight, based on the weight of the composition.

18. The composition of claim 1 wherein the electrolyte component is sodium chloride.

19. The composition of claim 1 wherein the electrolyte component is present in the composition in an amount of from about 0.5 to about 2% by weight, based on the weight of the composition.

20. The composition of claim 1 further comprising an additive selected from the group consisting of a formaldehyde-free preservative, a perfume, a dye, a pearlescent, and mixtures thereof.

21. A hair conditioning shampoo composition comprising:
   (a) from about 0.8 to about 1% by weight of a quaternized ester;
   (b) from about 0.8 to about 1% by weight of an emulsifier component;

(c) from about 9 to about 12% by weight of a betaine;

(d) from about 0.8 to about 1% by weight of an alkyl polyglycoside of formula I:

$$R_1O(R_2O)_b(Z)_a \qquad \text{I}$$

wherein $R_1$ is a monovalent organic radical having from about 12 to about 16 carbon atoms; $R_2$ is a divalent alkylene radical having from 2 to 4 carbon atoms; Z is a saccharide residue having 5 or 6 carbon atoms; b is 0; a is a number having a value of about 1.4;

(e) from about 0.8 to about 1% by weight of a Guerbet alcohol;

(f) from about 7 to about 8% by weight of a sodium lauryl ether sulfate having from 2 to 3 moles of ethylene oxide;

(g) from about 1.5 to about 2% by weight of a cocamide diethanolamide;

(h) from about 1 to about 1.5% by weight of sodium chloride; and (i) remainder, water, all weights being based on the weight of the composition.

22. A process for simultaneously conditioning and washing hair comprising contacting the hair with a hair conditioning shampoo composition comprising:

(a) a quaternary ammonium component;

(b) an emulsifier component;

(c) an amphoteric surfactant component;

(d) an alkyl polyglycoside of formula I:

$$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6;

(e) an emollient component;

(f) water;

(g) an anionic surfactant component;

(h) an amide component; and (i) an electrolyte component.

23. The process of claim 22 wherein the quaternary ammonium component is a quaternized ester.

24. The process of claim 23 wherein the quaternized ester is a dipalmitoleyl ethyl hydroxyethyl ammonium methyl sulfate.

25. The process of claim 22 wherein the quaternary ammonium component is present in the composition in an amount of from about 0.5 to about 1.5% by weight, based on the weight of the composition.

26. The process of claim 22 wherein the emulsifier is an ethoxylated fatty alcohol.

27. The process of claim 26 wherein the ethoxylated fatty alcohol is a cetearyl alcohol having 20 moles of ethylene oxide.

28. The process of claim 22 wherein the emulsifier component is present in the composition in an amount of from about 0.5 to about 2% by weight, based on the weight of the composition.

29. The process of claim 22 wherein the amphoteric surfactant component is a betaine.

30. The process of claim 22 wherein the amphoteric surfactant component is present in the composition in an amount of from about 5 to about 15% by weight, based on the weight of the composition.

31. The process of claim 22 wherein in formula I $R_1$ is a monovalent organic radical having from about 12 to about 16 carbon atoms, b is zero, and a is a number having a value of about 1.4.

32. The process of claim 22 wherein the alkyl polyglycoside is present in the composition in an amount of from about 2 to about 10% by weight, based on the weight of the composition.

33. The process of claim 22 wherein the emollient component is a Guerbet alcohol.

34. The process of claim 33 wherein the Guerbet alcohol is octyl dodecanol.

35. The process of claim 22 wherein the anionic surfactant component is sodium lauryl ether sulfate having from 2 to 3 moles of ethylene oxide.

36. The process of claim 22 wherein the anionic surfactant component is present in the composition in an amount of from about 5 to about 10% by weight, based on the weight of the composition.

37. The process of claim 22 wherein the amide component is cocamide diethanolamide.

38. The process of claim 22 wherein the amide component is present in the composition in an amount of from about 1.5 to about 2% by weight, based on the weight of the composition.

39. The process of claim 22 wherein the electrolyte component is sodium chloride.

40. The process of claim 22 wherein the electrolyte component is present in the composition in an amount of from about 0.5 to about 2% by weight, based on the weight of the composition.

41. The process of claim 22 further comprising adding an additive to the finished hair conditioning shampoo composition, the additive being selected from the group consisting of a formaldehyde-free preservative, a perfume, a dye, a pearlescent, and mixtures thereof.

42. The process of claim 22 wherein the finished hair conditioning shampoo composition has a viscosity ranging from about 3,500 to about 6,000 cps.

* * * * *